United States Patent [19]
Aeschlimann et al.

[11] Patent Number: 6,020,178
[45] Date of Patent: Feb. 1, 2000

[54] TRANSGLUTAMINASE AND GENE ENCODING SAME

[75] Inventors: Daniel P. Aeschlimann; Deane F. Mosher, both of Madison, Wis.

[73] Assignee: Wisconsin Alumni Research Foundation, Madison, Wis.

[21] Appl. No.: 09/257,799

[22] Filed: Feb. 25, 1999

Related U.S. Application Data

[62] Division of application No. 08/920,919, Aug. 29, 1997.

[51] Int. Cl.$^7$ ........................................... C12N 9/10
[52] U.S. Cl. ........................... 435/193; 435/183; 530/350
[58] Field of Search ..................... 435/193, 183; 530/350

[56] References Cited

U.S. PATENT DOCUMENTS 5,607,849  3/1997  Yasueda et al. .......................... 435/193

FOREIGN PATENT DOCUMENTS

| | | |
|---|---|---|
| 05023182 | 2/1993 | Japan . |
| 05056785 | 3/1993 | Japan . |
| 07023787 | 1/1995 | Japan . |
| 0925785 | 9/1997 | Japan . |
| WO 92/12238 | 7/1992 | WIPO . |

OTHER PUBLICATIONS

Aeschlimann, et al., "Isolation of a cDNA Encoding a Novel Member of the Transglutaminase Gene Family from Human Keratinocytes,"*The Journal of Biological Chemistry* 273:3452–3460 (1998).

Kim et al., "The Deduced Sequence of the Novel Protransglutaminase E (TGase3) of Human and Mouse," *The Journal of Biological Chemistry* 268:12682–12690 (1993).

Weraachakul–Boonmark, "Cloning and expression of chicken erythrocyte transglutaminase," *Biochemistry* 89:9804–9808 (1992).

*Primary Examiner*—Nancy Degen
*Attorney, Agent, or Firm*—Quarles & Brady LLP

[57] ABSTRACT

A pair of degenerate oligonucleotide primers can amplify transglutaminase-specific fragments of known transglutaminase genes. The primers are also used to obtain new transglutaminase gene products. The nucleotide sequence of a novel transglutaminase gene (termed $TG_x$) is presented.

2 Claims, 7 Drawing Sheets

```
                                              M   A   Q   G   L   E
      6
   human                          CAGCTACCATGGCCCAAGGGCTAGAA
     26

V   A   L   T   D   L   Q   S   S   R   N   N   V   R   H   H   T   E   E   I
     26
   human   GTGGCCCTCACAGACCTCCAGAGCTCCAGAAATAATGTGCGGCACCACACGGAGGAGATC
     86

T   V   D   H   L   L   V   R   R   G   Q   A   F   N   L   T   L   Y   F   R
     46
   human   ACTGTGGACCACCTGCTTGTTCGCCGGGGCCAGGCCTTCAACCTCACCCTGTACTTCAGG
    146

N   R   S   F   Q   P   G   L   D   N   I   I   F   V   V   E   T   .   E   D
     65
   human   AACCGGAGCTTCCAGCCAGGCCTGGACAACATCATCTTCGTGGTTGAAACT...GAGGAT
    203

A   V   Y   L   D   S   E   P   Q   R   Q   E   Y   V   M   N   D   Y   G   F
     85
   human   GCTGTCTACTTGGACAGTGAACCCCAGAGGCAGGAGTATGTCATGAATGATTATGGCTTC
    263

I   Y   Q   G   S   K   N   W   I   R   P   C   P   W   N   Y   G   Q   F   E
    105
   human   ATCTACCAAGGCAGCAAGAACTGGATCCGCCCATGTCCCTGGAACTATGGACAGTTTGAA
    323

D   K   I   I   D   I   C   L   K   L   L   D   K   S   L   H   F   Q   T   D
    125
   human   GACAAAATCATAGACATCTGCCTGAAGCTGCTAGACAAGAGCCTGCACTTCCAGACTGAC
    383

P   A   T   D   C   A   L   R   G   S   P   V   Y   V   S   R   V   V   C   A
    145
   human   CCAGCCACAGACTGTGCTCTGCGGGGAAGCCCCGTCTACGTCAGCAGAGTGGTGTGTGCC
    443

M   I   N   S   N   D   D   N   G   V   L   N   G   N   W   S   E   N   Y   T
    165
   human   ATGATCAACAGCAATGATGATAATGGGGTGCTCAATGGAAACTGGAGTGAGAATTACACA
    503

D   G   A   N   P   A   E   W   T   G   S   V   A   I   L   K   Q   W   N   A
    185
   human   GACGGCGCCAACCCTGCGGAGTGGACGGGCAGCGTGGCCATCCTGAAGCAGTGGAACGCC
    563

T   G   C   Q   P   V   R   Y   G   Q   C   W   V   F   A   A   V   M   C   T
    205
   human   ACAGGCTGCCAGCCCGTGCGCTACGGGCAATGCTGGGTCTTTGCTGCCGTCATGTGCACA
    623

V   M   R   C   L   G   I   P   T   R   V   I   T   N   F   D   S   G   H   D
    225
   human   GTGATGAGGTGTCTGGGGATCCCTACCCGTGTGATCACCAACTTCGACTCTGGCCACGAT
    683

T   D   G   N   L   I   I   D   E   Y   Y   D   N   T   G   R   I   L   G   N
    245
   human   ACAGATGGAAACCTGATCATAGATGAGTATTATGACAACACAGGCAGGATTTTGGGCAAT
    743

```
265                                             D  L  P  P  A  Y  G  G  W  Q  V  L  D  A  T  P  Q  E  M  S
human    AAGAAGAAGGATACTATCTGGAACTTCCATGTCTGGAATGAGTGCTGGATGGCCCGGAAG
803

D  L  P  P  A  Y  G  G  W  Q  V  L  D  A  T  P  Q  E  M  S
285
human    GATCTGCCCCCTGCATATGGAGGCTGGCAGGTGCTGGACGCCACACCTCAGGAGATGAGC
863

N  G  V  Y  C  C  G  P  A  S  V  R  A  I  K  E  G  E  V  D
305
human    AACGGCGTCTACTGCTGTGGCCCTGCCTCTGTCAGAGCCATCAAAGAAGGAGAAGTGGAC
923

L  N  Y  D  T  P  F  V  F  S  M  V  N  A  D  C  M  S  W  L
325
human    CTGAACTATGACACGCCCTTTGTGTTTTCGATGGTGAATGCTGACTGCATGTCCTGGCTC
983

V  Q  G  G  K  E  Q  K  L  H  Q  D  T  S  S  V  G  N  F  I
345
human    GTCCAGGGAGGGAAGGAGCAGAAGCTTCACCAGGACACGAGTTCTGTTGGCAATTTTATC
1043

S  T  K  S  I  Q  S  D  E  R  D  D  I  T  E  N  Y  K  Y  E
365
human    AGCACAAAGAGCATCCAGAGTGACGAGCGGGATGACATCACAGAGAACTACAAGTATGAA
1103
```

FIG 3A-2

```
              E   G   S   L   Q   E   R   Q   V   F   L   K   A   L   Q   K   L   K   A   R
385
human   GAAGGATCCCTCCAGGAGAGGCAGGTGTTTCTGAAGGCTCTGCAGAAGCTGAAGGCTAGA
1163

S   F   H   G   S   Q   R   G   A   E   L   Q   P   S   R   P   T   S   L   S
405
human   AGCTTCCATGGCTCCCAAAGAGGAGCAGAGTTGCAACCTTCCAGGCCCACATCACTGAGC
1223

Q   D   S   P   R   S   L   H   T   P   S   L   R   P   S   D   V   V   Q   V
425
human   CAGGACAGCCCTCGGAGCCTGCATACACCTTCCCTTCGACCCAGTGATGTGGTGCAAGTC
1283

S   L   K   F   K   L   L   D   P   P   N   M   G   Q   D   I   C   F   V   L
445
human   TCCCTGAAATTCAAGCTGCTCGACCCGCCCAACATGGGCCAGGATATATGCTTTGTCCTG
1343

L   A   L   N   M   S   S   Q   F   K   D   L   K   V   N   L   S   A   Q   S
465
human   CTGGCCCTCAACATGTCCTCCCAGTTCAAGGACCTCAAAGTGAACCTGAGTGCCCAGTCT
1403

L   L   H   D   G   S   P   L   S   P   F   W   Q   D   T   A   F   I   T   L
485
human   CTGCTGCACGATGGCAGCCCCCTGTCCCCATTCTGGCAGGACACAGCGTTCATCACACTC
1463

S   P   K   E   A   K   T   Y   P   C   K   I   S   Y   S   Q   Y   S   Q   Y
505
human   TCTCCTAAAGAAGCAAAGACCTACCCCTGCAAAATCTCCTATTCCCAGTACAGCCAGTAC
1523

L   S   T   D   K   L   I   R   I   S   A   L   G   E   E   K   S   S   P   E
525
human   CTGTCAACAGACAAGCTGATCCGCATCAGTGCCCTGGGTGAAGAGAAAAGCAGTCCTGAG
1583

K   I   L   V   N   K   I   I   T   L   S   Y   P   S   I   T   I   N   V   L
545
human   AAAATCCTGGTGAACAAGATCATCACCTTATCTTATCCAAGCATCACGATTAATGTTCTA
1643

G   A   A   V   V   N   Q   P   L   S   I   Q   V   I   F   S   N   P   L   S
565
human   GGAGCAGCCGTTGTGAACCAGCCACTCTCCATACAGGTGATATTTTCAAACCCCCTCTCG
1703

E   Q   V   E   D   C   V   L   T   V   E   G   S   G   L   F   K   K   Q   Q
585
human   GAGCAGGTTGAGGACTGTGTGCTGACTGTGGAAGGAAGTGGCCTCTTCAAGAAACAGCAG
1763

K   V   F   L   G   V   L   K   P   Q   H   Q   A   S   I   I   L   E   T   V
605
human   AAAGTCTTCCTTGGAGTCCTCAAACCCCAACACCAAGCAAGCATCATTCTGGAGACCGTC
1823

P   F   K   S   G   Q   R   Q   I   Q   A   N   M   R   S   N   K   F   K   D
625
human   CCCTTCAAGAGTGGACAAAGGCAGATCCAAGCTAATATGAGAAGCAACAAGTTTAAGGAC
1883

I   K   G   Y   R   N   V   Y   V   D   F   A   L och
```

FIG 3A-3

638
human    ATTAAGGGTTACAGGAATGTTTATGTAGACTTTGCATTA<u>TAA</u>ATTCTGGAACAACGCGCC
1943 human    AGACGTGTGAGTTTC
1958

FIG 3A-4

```
              .  G  P  L  S  D  L  A  L  G  T  R  A  V  F  S  L  A  R  H
   19
 human    ...GGACCGCTGTCAGACCTGGCCTTGGGGACTCGGGCTGTGTTCAGCCTGGCACGCCAT
   57

H  S  P  S  P  W  I  A  W  L  E  T  N  G  A  T  S  T  E  V
   39
 human    CACAGCCCCAGCCCCTGGATTGCCTGGCTGGAGACCAATGGGGCCACCTCCACAGAGGTG
  117

S  L  C  A  P  P  T  A  A  V  G  R  Y  L  L  K  I  H  I  D
   59
 human    AGCTTGTGCGCTCCTCCCACGGCGGCCGTGGGTCGGTACCTCTTGAAAATCCACATCGAC
  177

S  F  Q  G  S  V  T  A  Y  Q  L  G  E  F  I  L  L  F  N  P
   79
 human    TCCTTCCAGGGGTCTGTGACGGCCTACCAGCTAGGGGAGTTCATCCTGCTTTTCAATCCC
  237

W  C  P  .
   82
 human    TGGTGCCCA...
  246
```

FIG 3B

TRANSGLUTAMINASE AND GENE ENCODING SAME

CROSS-REFERENCE TO RELATED APPLICATIONS

This application is a divisional of copending application Ser. No. 08/920,919, filed Aug. 29, 1997.

STATEMENT REGARDING FEDERALLY SPONSORED RESEARCH OR DEVELOPMENT

This invention was made with United States government support awarded by the following agencies:
ARMY DOD Grant No: DAM17-96-1-6151
NIH Grants Nos: CA14520-22S1; CA14520-24; HL21644; HL49111; HL0784; and HL54462.
The United States has certain rights in this invention.

BACKGROUND OF THE INVENTION

Transglutaminases form a large family of protein cross-linking enzymes. Six transglutaminase gene products, mentioned below, have been characterized in higher vertebrates on the basis of their primary structure. Aeschlimann, D. and Paulsson, M. (1994) *Thromb Haemostasis* 71: 402–415. Enzymes of this class catalyze the $Ca^{2+}$-dependent transferase reaction (EC 2.3.2.13) which leads to the formation of an isopeptide bond between the γ-carboxamide group of a peptide-bound glutamine residue and various primary amines. Folk, J. E., and Finlayson, J. S. (1977) *Adv. Protein Chem.* 31: 1–133; Lorand, L., and Conrad, S. M. (1984) *Mol. Cell. Biochem.* 58: 9–35. Most commonly, γ-glutamyl-ε-lysine cross-links are formed in or between proteins by reaction with the ε-amino group of lysine residues. Analysis of the three-dimensional structure of the a-subunit of factor XIII showed that transglutaminases contain a central core domain containing enzymatic activity, and a N-terminal β-sandwich domain and two C-terminal β-barrel domains which are presumably involved in regulation of enzyme activity and specificity. Yee, V. et al. (1994) *Proc. Natl. Acad. Sci. U.S.A.* 91, 7296–7300. The catalytic core domain of transglutaminases is structurally related to the cysteine proteases and forms a similar catalytic triad, Cys-His-Asp, in the enzyme active site. This provides strong evidence for the transglutaminase cross-linking reaction being the reverse of the proteolytic cleavage reaction catalyzed by cysteine proteases. Yee, V. et al. (1996) *Sem. Thromb. Haemostasis* 22: 377–384. Transglutaminases undergo a number of post-translational modifications such as phosphorylation, fatty acylation, and proteolytic cleavage which regulate their enzymatic activity and sub-cellular localization. Aeschlimann, D. and Paulsson, M. (1994) *Thromb. Haemostasis* 71: 402–415.

Transglutaminase C ("$TG_c$"; tissue transglutaminase, transglutaminase type II) is expressed in many cell types and tissues in the vertebrate body, including endothelial cells, fibroblasts, macrophages, erythrocytes, chondrocytes, hepatocytes, smooth muscle cells, astrocytes, heart muscle, spleen, lung, eye lens, and various epithelia such as intestinal epithelia, tracheal epithelia, mucosal epithelia, mammary epithelia, kidney tubular epithelia, etc. Thomazy, V. and Fesus, L. (1989) *Cell Tissue Res.* 255: 215–224; Aeschlimann, D. and Paulsson, M. (1991) *J. Biol. Chem.* 266: 15308–15317; Gentile, V. et al., (1991) *J. Biol. Chem.* 266: 478–483; Weraarchakul-Boonmark, N. et al. (1992) *Proc. Natl. Acad. Sci. U.S.A.* 89: 9804–9808; Aeschlimann, D. et al. (1993) *J. Cell Biol.* 120: 1461–1470. In contrast to the other transglutaminase family members, the physiological function of $TG_c$ remains unclear and might be diverse in different tissues or biological events. $TG_c$ has been implicated in diverse processes such as stabilization of extracellular matrices in development and in wound healing, in apoptosis, and in receptor signaling. Aeschlimann, D. and Paulsson, M. (1991) *J. Biol. Chem.* 266: 15308–15317; Fesus, L. et al. (1991) *Eur. J. Cell Biol.* 56: 170–177; Aeschlimann, D. et al. (1995) *J. Cell Biol.* 129: 881–892; Nakaoka, H. et al. (1994) *Science* 264: 1593–1596.

Band 4.2 protein ("Band 4.2") is a membrane cytoskeleton component expressed at high level in erythroid cells. Korsgren, C. et al. (1990) *Biochemistry* 87, 613–617; Risinger, M. D, et al. (1992) *J. Biol. Chem.* 267, 5680–5685. Band 4.2 protein is the only member of this gene family that has lost the enzymatic activity to become a purely structural protein.

Platelets are the major source for factor XIII a-subunit ("FXIIIa") in plasma. Grundmann, U. et al. (1986) *Proc. Natl. Acad. Sci. U.S.A.* 83, 8024–8028; Takahashi, N. et al. (1986) *Proc. Natl. Acad. Sci. U.S.A.* 83, 8019–8023; Poon, M. et al. (1989) *J. Clin Invest* 84, 787–89. Platelets have been shown to contain mRNA transcripts even though they lack a nucleus, e.g. for FXIIIa (see below). Sottile, J. et al. (1989) *Thrombosis Haemost.* 62, 1100–1102. FXIIIa stabilizes the fibrin clot in haemostasis. Congenital deficiencies or acquired autoimmune response to factor XIII lead to a delayed bleeding tendency even though the primary haemostasis is normal due to insufficient clot stability. Board, P. G. et al. (1993) *Blood Rev.* 7: 229–242.

Transglutaminase K ("$TG_K$"; keratinocyte transglutaminase; transglutaminase type I) and transglutaminase E ("$TG_E$"; epidermal transglutaminase, transglutaminase type III) contribute to the formation of the cornified envelope in skin in distinct steps of keratinocyte differentiation. Kim, H. C. et al. (1991) *J. Biol. Chem.* 266: 536–539; Kim, I. G. et al. (1993) *J. Biol. Chem.* 268: 12682–12690; Kim, S. Y. et al. (1995) *J. Biol. Chem.* 270: 18026–18035. A congenital keratinization disorder, a distinct form of the heterogenous group of skin diseases referred to as autosomal recessive lamellar ichthyosis, has been linked to mutations in the gene coding for keratinocyte transglutaminase. Huber, M. et al. (1995) *Science* 267, 525–528.

Transglutaminase P ("$TG_P$"; prostate transglutaminase, transglutaminase type IV) is an androgen regulated protein involved in semen coagulation and its expression is restricted to prostate. Ho, D. C. et al. (1992) *J. Biol. Chem.* 267: 12660–12667; Grant, F. J. et al. (1994) *Biochem. Biophys. Res. Commun.* 203: 1117–1123; Dubbink, H. J. et al. (1996) *Biochem. J.* 315: 901–908.

A phylogenetic analysis of the transglutaminase genes indicates an early gene duplication event which subsequently gave rise to two different lineages; one including $TG_c$, $TG_E$, and Band 4.2 protein; the other, FXIIIa, $TG_K$, and likely also $TG_P$ (Aeschlimann and Paulsson, 1994).

Because more than one type of transglutaminase can be expressed in a single cell type (e.g., keratinocytes), and since the same gene product can be present in different cellular compartments, conflicting results have been reported about the nature of the transglutaminase enzymes involved in particular biological processes. What is desired is a sensitive and rapid diagnostic assay to determine the transglutaminases involved in particular biological events. Antibodies are not well suited for distinguishing among transglutaminases because of the potential cross reactivity among the different enzymes and the limited reactivity across species.

Extensive efforts have also been made to develop applications based on the unique ability of transglutaminases to cross-link proteins. Microbial transglutaminases have found use in food processing to add texture to processed foods, in particular processed meat. Food Research and Development Laboratories, Ajinomoto Co., Inc., Kanagawa, Japan. FXIIIa and more recently $TG_c$ have found applications as biological glues. Schlag, G., and Redl, H. (1988) *Clin. Orthop.* 227: 269–285; Martinowitz, U., and Schulman, S. (1995) *Thromb. Haemostasis* 74: 486–492; Juergensen, K. et al. (1997) *J. Bone Joint Surg.* 79-A: 185–193. Initially, FXIIIa was used as a cryoprecipitate from plasma, a product which carries an inherent risk of pathogen contamination. This has been overcome with the availability of recombinant FXIIIa. FXIIIa is also used therapeutically in patients deficient in factor XIII in the form of repeated intravenous injections. More recently, recombinant FXIIIa was also successfully used to treat chronic wound conditions such as ulcerative leg disease. Wozniak, G. et al. (1996), *Sem. Thromb. Haemostasis* 22: 445–450. Gene therapy with autologous bone marrow-derived stem cells transfected with an intact copy of the factor XIII gene might become an option for patients with a congenital deficiency of factor XIII. Similarly, the severe skin condition associated with $TG_K$ deficiency might be treated by gene therapy although the technology for the latter tissue is not as far developed. It is likely that the list of pathologies associated with deficiencies of transglutaminases will grow as additional information on the gene level becomes available. Thus, novel genetic therapies that employ recombinant versions of transglutaminase genes are also sought.

BRIEF SUMMARY OF THE INVENTION

The present invention is summarized in that a set of degenerate oligonucleotide primers can amplify DNA fragments that correspond to the highly-conserved active site region of proteins in the transglutaminase family. Each amplified fragment can be assigned to a particular transglutaminase gene because each contains restriction endonuclease cleavage sites not present in the other members of the gene family.

The invention is also summarized in that a novel transglutaminase gene, identified using the above-noted restriction endonuclease cleavage analysis, encodes an enzyme termed transglutaminase X ("$TG_X$"). The gene that encodes $TG_X$ is distinguished from the known transglutaminases in that it encodes a protein with a unique sequence. Human $TG_X$ furthermore includes a sequence that codes for approximately thirty amino acids inserted between the catalytic core domain and the C-terminal barrel domains not present in other transglutaminases.

It is an object of the present invention to provide a system for accurately distinguishing among the known transglutaminases expressed in a cell. It is another object of the present invention to detect expression of novel transglutaminase genes and proteins in cells.

It is an advantage of the present invention that the transglutaminase genes can be distinguished from one another by genetic differences rather than by less reliable immunological methods.

It is a feature of the present invention that degenerate probes flanking the highly conserved active site portion of transglutaminase genes can amplify fragments of various transglutaminase genes that can be distinguished on the basis of differences in their nucleic acid sequences.

Other objects, advantages, and features of the present invention will become apparent upon consideration of the following detailed description taken in conjunction with the accompanying drawings.

BRIEF DESCRIPTION OF THE SEVERAL VIEWS OF THE DRAWINGS

FIGS. 3A and 3B depict the sequence of TGx.

DETAILED DESCRIPTION OF THE INVENTION

Figure 1:
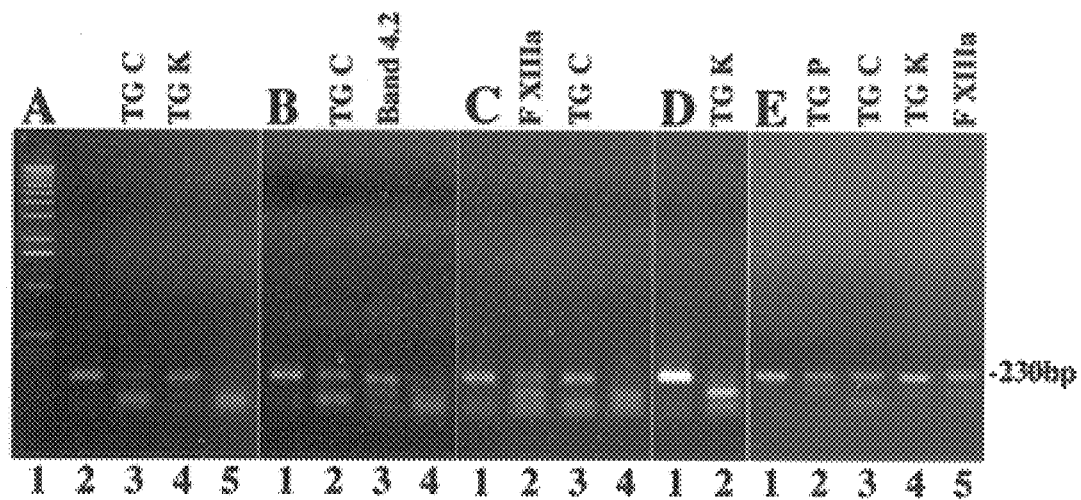
FIGS. 1A–E depict the fragments amplified using RT-PCR from various transglutaminase genes using degenerate primers according to the invention.

A single set of degenerate oligonucleotide primers can be used to amplify from messenger RNA unique fragments of DNA characteristic of particular transglutaminase genes. The bottom of Table 1 depicts suitable upstream and downstream primers, determined by comparing the sequences shown at the top of Table 1, that encode transglutaminase enzymes in humans, mice and rats. Where gene sequence from mouse and/or rat are available, these are compared directly to the corresponding human gene. Asterisks denote identity to the corresponding gene from humans.

TABLE 1

Degenerate primers for amplifying members of the transglutaminase gene
family by PCR.
h = human, m = mouse, r = rat, I = inosine.
Only human sequence is available for factor XIIIa.
The "upstream" sequences are shown as SEQ ID NOs:1–13 and the
"downstream" sequences are shown as SEQ ID NOs:14–26,
respectively, from top to bottom. Degenerate primer D1 is SEQ
NO:13; degenerate primer D2 is SEQ ID NO:26. Here, and
elsewhere in the application, where in the applicants are unable
to present the proper nucleotide in the Sequence Listing, the
applicants intend that the text of the specification is
controlling. For example, where inosine is used in an
embodiment, N is used in the Sequence Listing.

| Gene Products | Upstream Sequences and Derived Degenerate Primer D1 | Downstream Sequences and Derived Degenerate Primer D2 |
|---|---|---|
| $hTG_C$ (1) | TATGGCCAGTGCTGGGTCTTCGCCGCCGT | TGGATGACCAGGCCGGACCTGCAGCCGGG |
| $mTG_C$ (1) | \*\*C\*\*\*\*\*\*\*\*\*\*\*\*\*G\*\*T\*\*A\*\*G\*\* | \*\*\*\*\*\*\*\*\*\*\*\*\*\*A\*\*\*\*\*A\*\*\*\*\*\*\*\* |

TABLE 1-continued

Degenerate primers for amplifying members of the transglutaminase gene family by PCR.
h = human, m = mouse, r = rat, I = inosine.
Only human sequence is available for factor XIIIa.
The "upstream" sequences are shown as SEQ ID NOs:1–13 and the "downstream" sequences are shown as SEQ ID NOs:14–26, respectively, from top to bottom. Degenerate primer D1 is SEQ NO:13; degenerate primer D2 is SEQ NO:26. Here, and elsewhere in the application, where in the applicants are unable to present the proper nucleotide in the Sequence Listing, the applicants intend that the text of the specification is controlling. For example, where inosine is used in an embodiment, N is used in the Sequence Listing.

| Gene Products | Upstream Sequences and Derived Degenerate Primer D1 | Downstream Sequences and Derived Degenerate Primer D2 |
|---|---|---|
| hTG$_E$ (2) | TATGGCCAGTGCTGGGTCTTTGCTGGGAC | TGGTTTGTGAGGTCTGACCTGGGCCCCCC |
| mTG$_E$ (2) | *T************G****A | ***C*CA***A****A* |
| hB4.2 (3) | GATGGCCAGGCCTGGGTGTTGGCTGCTGT | TGGATGACGCGGCCTGCCTTGCCCCAGGG |
| mB4.2 (4) | GAC**G***CT**** | *****ACA*A**AT*T**A |
| hFXIIIa (5) | TATGGCCAATGCTGGGTTTTTGCTGGTGT | TGGATGACAAGGCCTGACCTTCCTGTTGG |
| hTG$_K$ (6) | TATGGCCAGTGCTGGGTCTTTGCTGGCGT | TGGATGAAGAGGCCGGATCTGCCCTCGGG |
| rTG$_K$ (6) | ******A**********CT | ************A*******A |
| hTG$_P$ (7) | TTTGGCCAGTGCTGGGTGTTTGCTGGGAT | TGGATGAAGCGACCCTACGACGGCTGCAG |
| rTG$_P$ (8) | **************TCT**AGT | ****AA*AGG*TCTACCCCAGG* |
| consensus | TATGGCCAGTGCTGGGT_TTTGCTGG_GT | TGGATGA_GAGGCC_GACCTGC_C___GG |
| sequence | Y G Q C W V F A G V | W M _ R P D L P _ G |
| degenerate | D1 | D2 |
| primer | TACGGCCAATGCTGGGTTTTCGCIGCAGT | CCAGGGIGAAGATCAGICCTCGCCATCCA |
| |     T       G        T     GG | G     C  G    T   TTT |
| (5'->3') | |        C     C     T |
| | |        T     T |

(1) Gentile et al., J. Biol. Chem. 266:478–483 (1991)
(2) Kim et al., J, Biol. Chem. 268:12682–12690 (1993)
(3) Korsgren et al., Biochemistry 87:613–617 (1990)
(4) Rybicki et al., Mamm. Genome 5:438–445 (1994)
(5) Grundmann et al., Proc. Natl. Acad. Sci. USA 83:8024–8028 (1986); Takahashi et al., Proc. Natl. Acad. Sci. USA 83:8019–8023 (1986)
(6) Philipps et al., Proc. Natl. Acad. Sci. USA 87:9333–9337 (1990); Kim et al., J. Biol. Chem. 266:536–539 (1991)
(7) Grant et al., Biochem. Biophys. Res. Commun. 203:1117–1123 (1194); Dubbink et al., Biochem. J. 315:901–908 (1196)
(8) Ho et al., J. Biol. Chem. 267:12660–12667 (1992)

The degenerate primers shown in Table 1 are to be considered preferred embodiments, but not the sole embodiments, of the invention. Of course, one skilled in the art, taking into account the nature of binding between primer and target, will appreciate that the preferred primer sequences can vary somewhat from those disclosed herein. What is important is that the primers be sufficiently related to the target that the desired portion of an expressed transglutaminase gene can be amplified and that the identity of the gene can be confirmed, for example in the manner disclosed herein. It will also be appreciated that variations in the target genetic material in a particular species may necessitate corresponding changes to the primer sequences.

One or more desired transglutaminase-specific DNA fragments can be amplified from mRNA in a reverse transcription—polymerase chain reaction using the primers of the present invention. Cellular messenger RNA that comprises one or more messenger RNA species that encode the generally highly conserved active site region of a transglutaminase protein is first reverse transcribed to make cDNA, in a manner known to the art. The cDNA is then used as a target for PCR amplification using the primers of the present invention.

The amplified PCR products can be analyzed by nucleic acid sequence analysis or by a standard restriction enzyme cleavage analysis to reveal different and distinct cleavage patterns for different transglutaminases, or to reveal heterogeneity in the population for one particular gene. Standard methods such as restriction fragment length polymorphism, or any other such method now known or in the future developed, may be suitable for diagnostic prediction.

Each amplified fragment can be separately cloned. The fragments can be advantageously cloned using a system that takes advantage of A-overhangs produced by various DNA polymerases, e.g., Taq polymerase, for example the TA-Cloning Kit commercially available from Invitrogen. The DNA sequence of each clone can then be determined to confirm its identity. To facilitate cloning of rare PCR products, the mixture of amplified DNA fragments from different transglutaminases can be cleaved with a characteristic restriction enzyme to degrade predominant known PCR products (see following paragraphs), with the remaining fragments being cloned as above. The working example confirms the reliability of the assay, in that the expected type(s) of transglutaminase is detected and shown to be expressed in each appropriate cell type.

It is preferred that the fragment amplified from each of the transglutaminase genes can also, or alternatively, be characterized by cleavage with a single restriction enzyme that cleaves at a characteristic restriction site in the amplified fragment. It is likewise preferred that the selected enzyme not cleave the other members of the transglutaminase gene family. It is also preferred that the specificity of the selected restriction site be conserved between species for a particular transglutaminase gene.

Each amplifiable transglutaminase gene can be assigned one or more restriction enzyme that cleaves the amplified fragment, but does not cleave the fragments amplified from other members of the gene family. Table 2 shows a preferred list of such enzymes for the known transglutaminase enzymes. Although this selection of restriction enzymes will likely apply to the transglutaminase genes of most higher vertebrate species, one of ordinary skill will understand that a sequence comparison should be performed for each species under study, because of the significant level of sequence variation at the nucleotide level between species.

TABLE 2

Restriction enzymes for
identifying transglutaminase gene products

| Transglutaminase Gene | Selected Enzyme(s) |
|---|---|
| $TG_C$ | ScaI |
| $TG_E$ | BclI or AvaI, and NcoI |
| Band 4.2 | BstEII |
| FXIIIa | EcoRI |
| $TG_K$ | Bsp1286I and NcoI |
| $TG_P$ | Tth111I |

As is detailed in the example below, the preceding analysis can also reveal previously unknown genes that are expressed. A novel gene termed $TG_X$ was uncovered using this method. A fragment amplified from RNA by RT-PCR exhibited a restriction enzyme cleavage pattern different from that of the known transglutaminase genes. Upon further analysis, detailed below, it became apparent that the novel cDNA differs from the known transglutaminases in its primary sequence and in its splicing pattern. Thus the present invention includes both a method for readily characterizing known transglutaminase genes, and a method for obtaining novel transglutaminase genes, as well as the novel genes themselves.

The present invention also provides an ability to produce a transglutaminase and polypeptides or fragments thereof by recombinant means, preferably in cultured eukaryotic cells. The expressed transglutaminase may or may not have the biological activity of the native enzyme, depending upon the intended use. Accordingly, isolated and purified polynucleotides are described which code for the transglutaminases and fragments thereof, where the polynucleotides may be in the form of DNA, such as cDNA or genomic DNA, or RNA. Based on these sequences probes may be designed for hybridization to identify these and related genes or transcription products thereof which encode transglutaminases or fragments thereof. The genomic equivalents of the gene or genes can be obtained and characterized.

In related embodiments, the invention concerns DNA constructs which comprise a transcriptional promoter, a DNA sequence which encodes the transglutaminase or fragment thereof, and a transcriptional terminator, each operably linked for expression of the enzyme or enzyme fragment. The transglutaminase genes can be inserted (in whole or in part) into genetic constructs using methods known to the art. The constructs are preferably used to transform or transfect host cells, including bacterial cells, but preferably eukaryotic cells, more preferably yeast or mammalian cells or in a non-cellular expression system. For large scale production, the expressed transglutaminase may be isolated from the cells by, for example, affinity purification.

The protein can be expressed in situ for therapeutic purposes or can be purified in a manner known to the art for subsequent formulation into therapeutic or cosmetic products for topical or internal use. Nucleic acid sequences that encode the transglutaminase of the invention may be used for genetic therapy in people having a functional deficit in crosslinking, as observed in patients suffering from lamellar ichthyosis, or in people having other conditions relating to a transglutaminase having aberrant function. The recombinant transglutaminases themselves may be applied topically, e.g., on skin lesions, to facilitate wound closure.

It is also understood that the sequence encoding the transglutaminase to be expressed by recombinant means can have an altered sequence relative to the nucleic acid obtained from either a cDNA or from genomic DNA. The art understands that certain changes in nucleic acid sequence make little or no difference to the overall function of the protein or peptide encoded. For example, conservative changes, particularly in the third positions of codons, may not affect the specified amino acid. Other changes may result in an amino acid substitution which has little or no effect upon the three dimensional structure or function of the encoded protein or peptide. In addition, changes that result in insertions or deletions of amino acids may also be acceptable.

Thus, when producing a transglutaminase by recombinant means, it may be desirable in accordance with the desired use to substitute, insert or delete amino acids from the transglutaminase. Such changes can be achieved in the nucleic acid using site-directed mutagenesis methods that are well-known to the molecular biologist. Such changes are considered to be within the scope of the present invention. Exemplary reasons for such changes include modulating certain properties such as catalytic activity, stability to changed in pH and temperature, and altering storage stability or half life.

It is also understood that the nucleic acid encoding the transglutaminase or fragment thereof can be combined in a recombinant expression vector with sequences that can modulate expression, for example, secretion of the encoded transglutaminase. Also, tags that can enhance detection of the encoded proteins or fragments can be added.

The invention can be applied in any animal species having transglutaminases, but the invention finds particular application in humans and other mammals and in animal systems used in the art to model the human. These include, but are not limited to, xenopus, drosophila, zebrafish and mouse.

The present invention will be further understood by reference to the following non-limiting example.

EXAMPLE

Design of PCR Primers for Amplifying Transglutaminase Gene Products—When the different known transglutaminase gene products were aligned and compared at the nucleotide level, several conserved regions were observed that could serve as targets for primers, particularly in the catalytic core domain (Table I). By PCR screening oligonucleotide primers derived from various conserved regions and plasmid DNA substrates encoding various transglutaminases, a single set of degenerate oligonucleotide primers (Table I) were identified that amplified a DNA fragment encoding the highly conserved active site region of transglutaminases visible as a single dominant band when analyzed by agarose gel electrophoresis with ethidium bromide staining (FIG. 1). The degenerate oligonucleotide primers D1 and D2 are based on the amino acid sequence YGQCWVFAGV (translation of SEQ ID NO:12), which includes the active site cysteine residue, and WM_RPDLP_G (translation of SEQ ID NO:25) (Table I).

Initial attempts with shorter oligonucleotides (18 bp) based upon the conserved sequences LFNPWC (SEQ ID NO:29), QCWVFA (SEQ ID NO:30), and WNFHVW (SEQ ID NO:31) were unsuccessful. Also, degenerate oligonucleotides based on the sequence WQ_LDATPQE (SEQ ID NO:32) and F_LLFNPWC (SEQ ID NO:33) did not yield PCR products.

Cells—Primary human keratinocytes were isolated from neonatal human foreskin as described previously (Allen-Hoffmann, B. L., and Rheinwald, J. G., *Proc. Natl. Acad. Sci. U.S.A.*, 81: 7802–7806 (1984)). Primary keratinocyte cultures were established on mitomycin-C treated mouse Swiss 3T3 fibroblast feeder layers in 3 parts Ham's F12 plus 1 part Dulbecco's Modified Eagle's medium containing 2.5% fetal bovine serum, 0.4 µg/ml hydrocortisone, 8.4 ng/ml cholera toxin, 5 µg/ml insulin, 24 µg/ml adenine, 10 ng/ml epidermal growth factor (EGF; R&D Systems, Minneapolis, Minn.) and antibiotics (100 µg/ml streptomycin and 100 units/ml penicillin).

To induce differentiation, cells were harvested by trypsinization and cultured for the indicated time in suspension in the same medium supplemented with 1.68% methylcellulose (4,000 centipoises; Fisher Scientific Corp., Pittsburgh, Pa.) (Hines, M. D., and Allen-Hoffmann, B. L., *J. Biol. Chem.* 271: 6245–6251 (1996)). For experiments analyzing the effect of cell density and growth factors on differentiation, cells were grown for one passage on a feeder layer in the absence of EGF. Subsequently, cells were grown for 24 h without a feeder layer before supplementing the medium with 0.5 nM EGF, 0.5 nM keratinocyte growth factor (KGF; Promega), or 10 µl of 0.1% bovine serum albumin (BSA)/ml medium for the indicated time (Hines, M. D., and Allen-Hoffmann, B. L., *J. Biol. Chem.* 271: 6245–6251 (1996)).

Human dermal fibroblasts, TJ6F, were established from trypsinized foreskin tissue, human osteosarcoma cell line MG-63 (CRL 1427) and human fibrosarcoma cell line HT1080 (CCL 121) were purchased from the American Type Culture Collection (ATCC, Rockville, Md.), and were cultured in Dulbecco's Modified Eagle's medium containing 10% fetal bovine serum and antibiotics.

Human erythroleukemia cell line HEL was kindly provided by Dr. Mortimer Poncz, Philadelphia, Pa., cultured in suspension in RPMI 1640 medium containing 12% fetal bovine serum, 1 mM pyruvate and antibiotics, and induced to differentiate with 1.25% dimethyl sulfoxide for 2 days (Martin, P., and Papayannopoulou, T., *Science,* 216: 1233–1235 (1982)).

Human platelets were collected as described (Sottile, J. et al., *Thrombosis Haemost,* 62: 1100–1102 (1989)), and a contamination with leukocytes or red blood cells was ruled out by phase contrast microscopy.

Amplifying transglutaminase—specific sequences by PCR using degenerate primers—Poly(A)$^+$ RNA was obtained from about $10^6$ cells or 10 µg total RNA by oligo(dT)-cellulose column chromatography using the Micro-Fast Track Kit (Invitrogen, San Diego, Calif.) and was recovered in 20 µl 10 mM Tris/HCl, pH 7.5. The poly(A)$^+$ RNA (5.0 µl) was reverse transcribed into DNA in a total volume of 20 µl using the cDNA Cycle Kit (Invitrogen) with either 1.0 µl of random primers (1 µg/µl) or oligo(dT) primer (0.2 µg/µl). No difference in the amount or nature of the PCR-product was observed when the reverse transcription was done with random or oligo(dT) primers. cDNA from human prostate carcinoma tissue was kindly provided by Dr. Erik J. Dubbink, Rotterdam, The Netherlands (Dubbink, H. J. et al., *Biochem. J.,* 315: 901–908 (1996)).

PCRs were carried out with 2.5 units of Taq DNA polymerase (Fisher Sci.) and 25% of the reverse transcriptase reaction mixture (5.0 µl) in 100 µl of 10 mM Tris/HCl, pH 8.3, 50 mM KCl containing 2 mM $MgCl_2$, 0.2 mM dNTPs and 50 pmol of the transglutaminase-specific degenerate oligonucleotide primers D1 and D2 (Table I). The PCR cycles were 45 sec at 94° C. (denaturation), 2 min at 55° C. (annealing), and 3 min at 72° C. (elongation). A total of 37 cycles were made, with the first cycle containing an extended denaturation period (6 min) during which the polymerase was added (hot start), and the last cycle containing an extended elongation period (10 min).

A 230 bp fragment corresponding to the active site of transglutaminases was amplified with degenerate primers D1 and D2 (Table 1 and FIG. 1) by RT-PCR from A)MG-63 osteosarcoma cells (lane A2), B) HEL erythroleukemia cells (lane B1), C) platelets (lane C1), D) keratinocytes (lane D1) and E) prostate carcinoma tissue (lane E1). Cleavage of the PCR-products with restriction enzymes revealed the type of transglutaminase expressed: Sca I, $TG_c$; BstE II, band 4.2 protein; EcoR I, factor XIII a-subunit; Bsp1286 I, $TG_K$; and Tth111 I, $TG_p$. In osteosarcoma cells, ScaI (lane A3), Bsp1286 I (lane A4), and Sca I+Bsp1286 I (lane A5) reveal $TG_c$ and $TG_K$; in erythroleukemia cells, Sca I (lane B2), BstE II (lane B3), and Sca I+BstEII (lane B4) reveal $TG_c$ and band 4.2 protein; in platelets, EcoR I (lane C2), Sca I (lane C3), and EcoR I+Sca I (lane C4) reveal factor XIIIa and $TG_c$; in keratinocytes; Bsp1286 I (lane D2) reveals $TG_K$; and in prostate carcinoma tissue; Tth111 I (lane E2), Sca I (lane E3), Bsp1286 I (lane E4), and EcoR I (lane E5) reveal $TG_p$, $TG_c$, $TG_K$, and factor XIIIa. DNA-fragments were analyzed by electrophoresis in 1% agarose gels calibrated with the 1 kb-DNA ladder (lane AI; Gibco BRL).

The PCR products were purified by agarose gel electrophoresis, recovered with the Wizard PCR Preps DNA Purification System (Promega) and cloned by taking advantage of the 3' A-overhangs generated by Taq DNA polymerase using the Original TA-Cloning Kit (Invitrogen). Plasmid DNA was prepared with the Wizard Minipreps DNA Purification System (Promega) and sequencing performed by the dideoxy chain termination method using the Sequenase Version 2.0 Kit (United States Biochemical, Cleveland, Ohio). Clones containing amplified DNA sequences derived from the predicted transglutaminase gene were obtained in each case.

The observed expression profiles are shown in Table 3. The only departure from the expected expression pattern of transglutaminases in the various cell types was an unexpected PCR product that did not conform to any of the expected cleavage patterns of the previously characterized transglutaminase gene products. The novel gene corresponding to this product is termed Transglutaminase X or $TG_X$. $TG_X$ was initially discovered in cultured human keratinocytes from neonatal foreskin, but $TG_X$ was also present in a commercial cDNA library made from fetal human skin (18 weeks gestation, Invitrogen).

primers (antisense) "r". The following abbreviations are used for degenerate positions in oligonucleotides: M=A,C; R=A,G; S=C,G; W=A,T; Y=C,T; I=inosine.

To exclude sequence mutations introduced by Taq DNA polymerase, all DNA fragments were amplified at least twice in independent reactions, and the sequences of the cloned PCR products from several bacterial clones were compared.

TABLE 4

Sequences of primers used for PCR of $TG_X$ (SEQ ID NOs: 34–44, respectively, top to bottom)

| Designation | Sequence | Orientation | Position |
|---|---|---|---|
| D3 | 5'-CTCTCYTCIICISWICCYTCTGGGWAYTTGTA | r | 1092–1123 |
| D4 | 5'-TGGAIIAIGARGAIGAGMGRSARGARTATGT | f | 214–244 |
| S1 | 5'-TAGATGAGTATTATGACAACACAGGCAGG | f | 703–731 |
| S2 | 5'-AGGATTTTGGGGAATAAGAAGAAGGATAC | f | 729–757 |
| S3 | 5'-TCCTTCTTCTTATTCCCCAAAATCCTGCC | r | 726–754 |
| S4 | 5'-TTCACCAGGACACGAGTTCTGTTGGCA | f | 1009–1035 |
| S5 | 5'-CAAAGAGCATCCAGAGTGACGAGCGGG | f | 1048–1074 |
| S6 | 5'-TCTGTGGCTGGGTCAGTCTGGAAGTGC | r | 368–394 |
| S7 | 5'-TGTCIATAGTTICAGGGAIATGGGCGG | r | 290–316 |
| S8 | 5'-CAGTTCTTGCTGCCTTGGTAGATGAAGCC | r | 258–286 |
| S9 | 5'-GGGCTGTCCTGGCTCAGTGATGTGGGC | r | 1208–1234 |

TABLE 3

| Cell Type | $TG_C$ | Band 4.2 | $TG_K$ | Factor XIIIa | $TG_E$ | $TG_P$ |
|---|---|---|---|---|---|---|
| Primary dermal fibroblasts | + | | | | | |
| Fibrosarcoma HT 1080 | + | | | | | |
| Osteosarcoma MG-63 | + | | + | | | |
| Erythroleukemia Cell line HEL | + | + | | | | |
| Platelets | + | | | + | | |
| Primary Keratinocytes (induc. to diff) | +* | | + | | n.d.** | |
| Prostate carcinoma tissue | + | | + | + | | + |

*only in adherent cells (prior to induction of differentiation)
**Not detected. TGE i5 only found in epidermis and hair follicles; not detectable in primary human keratinocytes, see also Kim et al, J. Biol. Chem 268:12682–12690 (1993)

Figure 2:
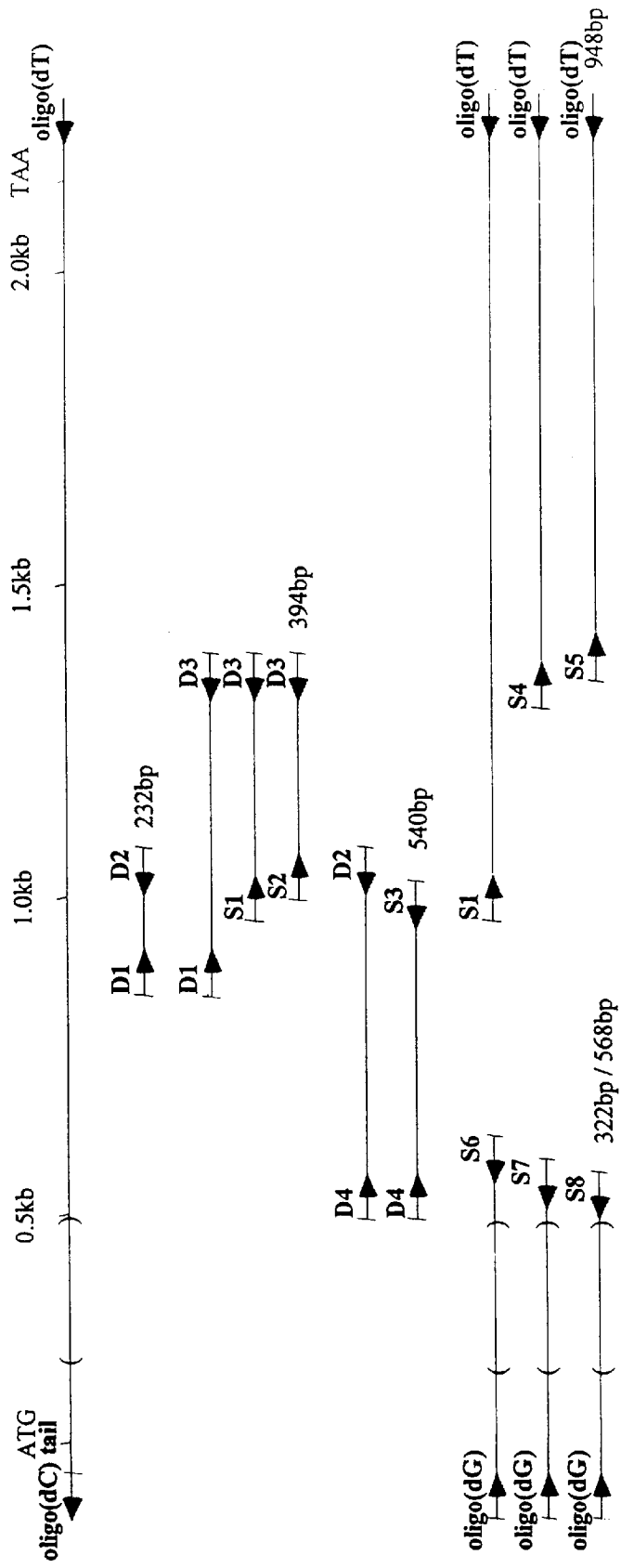
FIG. 2 depicts a strategy for amplifying fragments of the novel transglutaminase X gene.

Cloning $TG_X$ from human keratinocytes by anchored PCR and its deduced amino acid sequence—To obtain further sequence information on $TG_X$, oligo(dT) primed double stranded cDNA was prepared from poly(A)+ RNA from primary keratinocytes isolated from human foreskin. The strategy of the anchored PCR is summarized in FIG. 2, and the sequence of the oligonucleotide primers is given in Tables 1 and 4. Primers were numbered and were used for amplification of $TG_X$ specific sequences as indicated in FIG. 2. "D" indicates degenerate primer; "S", $TG_X$ specific primer. Forward primers (sense) are labeled "f", reverse The upper line in FIG. 2 represents the cDNA for $TG_X$ with the start and stop codon indicated. Brackets indicate an alternatively spliced sequence located toward the 5' end of the coding region. Below is an outline of the PCR strategy, showing the consecutive PCR reactions performed with nested oligonucleotide primers to obtain PCR products that can be visualized in ethidium bromide-stained agarose gels. The length of the final PCR products is given on the right. The oligo(dT)-Not I unidirectional primer (Invitrogen), 5'-AACCCGGCTCGAGCGGCCGCT$_{(18)}$ (SEQ ID NO:45), was used as the 3' anchoring primer. The abridged anchor primer (Gibco BRL), 5'-GGCCACGCGTCGACTAGTACGGGIIGGGIIGGGIIG (SEQ ID NO:46), was used as the 5' anchoring primer. In this case, the subsequently used primer for nested PCR was a shortened oligonucleotide, universal amplification primer (Gibco BRL), which included the first 20 nucleotides of the abridged anchor primer.

Briefly, sequences of the 3'-end of $TG_X$ were amplified by consecutive PCR reactions using degenerate primer D1 and $TG_X$-specific primers S1 and S2 together with degenerate primer D3 which is derived from the conserved amino acid sequence YKYPEGS_EER (Amino acids 443 to 453 in $TG_X$). The residual 3'-sequence was amplified by sequential PCR reactions using $TG_X$-specific primers S1, S4 and S5 in combination with the oligo(dT)-Not I primer used for cDNA priming. Sequences 5' to the active site were amplified in consecutive PCR reactions using degenerate primer D2 and $TG_X$-specific primer S3 together with degenerate oligonucleotide D4 which is based on an upstream cluster of conserved amino acids, i.e. LD_E_ER_EYV (Amino acids 150 to 160 in $TG_X$).

Attempts to amplify sequences upstream of primer D4 with additional degenerate oligonucleotides failed. To obtain more information on the 5' end of $TG_X$, a 5'-RACE approach (Frohman, M. A. et al., Proc. Natl. Acad. Sci. U.S.A. 85: 8998–9002 (1988)) was used. A poly(dC) tail was added to the cDNA using terminal deoxynucleotidyl transferase to anchor the PCR reaction with an oligo(dG) primer (abridged anchor primer). Subsequent reactions with nested primers yielded $TG_X$ related PCR products (see FIG. 2).

Heterogeneity of the sequence upstream of primer D4 was encountered, causing considerable difficulties in obtaining 5' sequence. Three different sequences have been obtained upstream of the sequence EDAVY (Amino acids 145 to 149 in $TG_X$). Two $TG_X$ sequences, a long form and a short form, have been characterized and are described below. In FIG. 3, the full length sequence of the short version of $TG_X$ is shown (3A) with dots marking the position of the 82 amino acid insert (3B) in the long version. The initiation and termination codons are underlined. (See also SEQ ID NO:47 which shows the long version of the $TG_X$ cDNA and SEQ ID NO:48 which shows the translation of that sequence. The initial methionine shown in SEQ ID NO:47 and 48 is not present in the mature protein, so references herein to particular amino acid numbers in the mature protein are offset by 1 from the numbers shown in the Sequence Listing, unless otherwise noted. The portion that is spliced out in the short form cDNA is between bases 198 and 443 of SEQ ID NO:47. The primer binding sites for D1 and D2 are shown at nucleotides 831–860 and 1035–1066 of SEQ ID NO:47, respectively).

The short form of $TG_X$ sequence contains at least 1958 nucleotides which includes an open reading frame of 1914 base pairs. The long form of $TG_X$ contains at least 2204 nucleotides with an open reading frame of 2160 base pairs. The initiation codon is present in a consensus sequence (ACC<u>ATG</u>G) identified as a signal for efficient translation in higher eukaryotes (Kozak, 1986). No polyadenylation signal (AATAAA) was recognized in the short 3'-untranslated region following the termination codon (TAA), indicating that it might be incomplete. However, repeated synthesis of double stranded cDNA and PCR with different primers under various conditions did not yield additional 3' sequence. All isolated cDNAs end within 9 to 34 nt downstream of the pentanucleotide ATAAA at position 1922, i.e. at position 1935, 1938, 1939, 1942, 1943, and 1958. This pentanucleotide has been shown to function as a polyadenylation signal in other genes (Berget, S. M., *Nature* 309: 179–182 (1984)) and could be functional in $TG_X$, giving rise to a very short 3' untranslated region.

The deduced protein for the short form of $TG_X$ consists of 638 amino acids and has a calculated molecular mass of 71,915 Da and an isoelectric point of 5.9. The deduced protein for the long form of $TG_X$ consists of 720 amino acids and has a calculated molecular mass of 80,764 Da and an isoelectric point of 6.0.

Expression of novel $TG_X$ and other transglutaminase genes in human keratinocytes—cDNA probes spanning the sequence that encodes the two C-terminal barrel domains of different human transglutaminases were used to detect the novel $TG_X$ and other transglutaminase gene products known to be expressed in keratinocytes on a Northern blot of human foreskin mRNA. Northern blot containing 3 μg of poly (A)⁺ RNA from adherent keratinocytes was probed consecutively with a ~700 bp fragment that contained the two C-terminal beta barrel domains of $TG_X$, $TG_K$, and $TG_c$. The blot was exposed for 3 days ($TG_X$), 4 hours ($TG_K$), or 4 days ($TG_c$). mRNA's of the expected sizes were detected for $TG_c$, 3.7 kb, and $TG_K$, 2.7 kb (Gentile, V. et al., *J. Biol. Chem.*, 266: 478–483 (1991); Kim, H. C. et al., *J. Biol. Chem.*, 266: 536–539 (1991)). Two different mRNA's with a size of about 2.2 and 2.8 kb were detected for $TG_X$, indicating that alternative processing of the $TG_X$ transcript occurs. The smaller transcript of $TG_X$ is likely identical to a band of approximately 2.4 kb that had been previously detected with a degenerate oligonucleotide on a Northern blot of human foreskin RNA which was assumed to be band 4.2 protein based on its size (Kim, I. G. et al., *J. Biol. Chem.*, 268: 12682–12690 (1993)). This is further supported by the fact that the transcript for band 4.2 protein could not be detected with a specific probe. The probes displayed no significant cross-hybridization as indicated by the distinct migration of the detected mRNA's for the different gene products in the gel. The relative abundance of the transcripts for $TG_X$:$TG_K$: $TG_c$ is about 3:80:1. This corresponds well with the results from the PCR amplification of transglutaminases using the degenerate primers D1 and D2.

The cDNA sequence of the short form of $TG_X$ is identical to the sequence of the long form except that the short form lacks the sequence encoded by exon III in other transglutaminase genes (Table 5). The splice donor and acceptor sites for the short and long form of $TG_X$ are based on the cDNA sequences and are represented in Table 5 in alignment with known splice sites in other transglutaminase genes. The $TG_X$ long donor and acceptor sequences are shown at bases 435–443 and 444–485 of SEQ ID NO:47, respectively. The $TG_X$ short donor and acceptor sequences are shown at bases 189–197 and 444–485 of SEQ ID NO:47, respectively. Donor and acceptor sequences for h$TG_c$, h$TG_E$, and human Band 4.2 are shown as SEQ ID NOs:49 and 50, SEQ ID NOs:51 and 52, and SEQ ID NOs:53 and 54, respectively. Residues consistent with the splice site consensus sequence (MAG/GTRAG and YAG/G) are underlined. The sizes of the mRNA's of $TG_X$ are larger than expected from sequencing data. This is most likely due to the presence of additional 5' or 3' non-coding sequences. The smaller, more abundant mRNA might result from alternative splicing of the sequence encoded by exon III. Alternatively spliced mRNA's have been described for $TG_c$ (Fraij, B. M. et al., *J. Biol. Chem.*, 267: 22616–22623 (1992); Monsonego, A. et al., *J. Biol. Chem.*, 272: 3724–3732 (1997)), band 4.2 protein (Korsgren, C. and Cohen, C. M., *Proc. Natl. Acad. Sci. U.S.A.*, 88: 4840–4844 (1991); Sung, L. A. et al., *Blood*, 79: 2763–2770 (1992); Cohen, C. M. et al., *Sem. Haematology*, 30: 119–137 (1993)) and $TG_P$ (Thelen, K., Zippelius, A., Oberneder, R., Rietmueller, G., and Pantel, K.: Genbank #U79008). No common pattern for alternative splicing is evident from the current data, and different exons are apparently alternatively processed in the different gene products. However, a band 4.2 isoform lacking exon III has been found in endothelial cells (Cohen, C. M. et al., *Sem. Haematology*, 30: 119–137 (1993)), and a putative $TG_P$ isoform lacks part of exon III (Thelen, K., Zippelius, A., Oberneder, R., Rietmueller, G., and Pantel, K.: Genbank #U79008).

TABLE 5

| Gene Product | Donor Sequence | Exons | Acceptor Sequence |
|---|---|---|---|
| hTG$_X$ long | W C P<br>TGGTGCC<u>CAG</u> | III/IV? | E D A V<br>AGGATGCTGTC |
| hTG$_X$ short | V E T<br>GTTGAA<u>A</u>CTG | II/IV? | E D A V<br>AGGATGCTGTC |
| hTG$_C$ (1) | W C P<br>TGGTGCC<u>CAG</u>gtgagccaca | III/IV | A D A V<br>CGGATGCTGTG |
| hTG$_E$ (2) | W L N<br>TGGCTGA<u>AT</u>Ggtaggtgtct | III/IV | V D S V<br>tatcaaa<u>tag</u>TGGATAGCGTC |
| hB4.2 (3) | W N R<br>TGGAATAG<u>A</u>Ggtaagtttga | III/IV | E D A V<br>ctctcac<u>cag</u>AGGATGCTGTG |

(1) Lu et al., J. Biol. Chem. 270:9748–9756 (1995)
(2) Kim et al., J. Invest. Dermatol. 103:137–142 (1994)
(3) Korsgren and Cohen, Proc. Natl. Acad. Sci. USA 88:4840–4844 (1991)

To analyze the expression of TG$_X$ in relation to terminal differentiation of keratinocytes, normal human keratinocytes were induced to differentiate by culture in suspension in a semi-solid methylcellulose medium. A 225 bp fragment of TG$_X$ was amplified by RT-PCR using TG$_X$ specific primers S4 and S9 (Table 4) from an identical amount of poly(A)$^+$ RNA from dermal fibroblasts, HT180 fibrosarcoma cells, MG-63 osteosarcoma cells, platelets, HEL erythroleukemia cells, adherent and non-adherent keratinocytes, and a fetal human skin cDNA library (18 weeks gestation, commercially available from Invitrogen). Normal human keratinocytes were analyzed either prior to (adherent) or after culture in suspension for 4 h (non-adherent). PCR products were analyzed by electrophoresis in 1% agarose gels calibrated with the 1 kb-DNA ladder (Gibco BRL).

TG$_X$ was detected in keratinocytes, osteosarcoma cells and erythroleukemia cells. Even though TG$_X$ was present in adherent keratinocytes, it appeared to be induced in cells triggered to differentiate by culture in suspension. To corroborate this result, the expression of TG$_X$ was analyzed by semi quantitative PCR in preconfluent and postconfluent keratinocyte cultures in the presence or absence of either EGF or KGF. EGF is well known to support keratinocyte growth, while KGF has recently been shown to attenuate differentiation specifically in hyperconfluent keratinocyte cultures (Hines, M. D. and Allen-Hoffmann, B. L. J. Biol. Chem., 271: 6245–6251 (1996)). Normal human keratinocytes were treated with BSA, 0.5 nM EGF, or 0.5 nM KGF in standard medium for 3 days (preconfluent) or 10 days (postconfluent). Sequences for all transglutaminases were amplified by RT-PCR with degenerate primers D1 and D2. Amplification of a sequence specific for TG$_X$ was done with specific primers S4 and S9. Amplification of a sequence specific for glyceraldehyde 3-phosphate dehydrogenase with a control primer set (600 bp fragment; Stratagene) confirmed that equal amounts of message were present in the different samples. All primer sets span intron-exon boundaries thereby ensuring that the PCR products are derived from mRNA. PCR products were analyzed in 1% agarose gels.

A several fold increase in TG$_X$ expression was associated with cell-density-induced differentiation, and a reduction in TG$_X$ expression was observed in KGF-treated, as compared to untreated, cultures. Amplification of transglutaminases with the degenerate oligonucleotides showed the same general pattern, although the treatment effect was even more pronounced. The latter result is consistent with the pattern of transglutaminase activity measured in these cultures (Hines, M. D. and Allen-Hoffmann, B. L. J. Biol. Chem., 271: 6245–6251 (1996)) and is likely to reflect largely the expression of TG$_K$ which is the keratinoant type of enzyme expressed in keratinocytes.

Structural features of TG$_X$—A comparison of TG$_X$ with the previously characterized transglutaminases reveals that the structural requirements for transglutaminase activity and Ca$^{2+}$ binding are conserved in TG$_X$. The overall sequence identity between TG$_X$ and TG$_C$, TG$_E$, band 4.2 protein, FXIIIa, TV$_K$ or TG$_P$, is 40.1%, 42.3%, 31.6%, 32.7%, 34.9%, and 31.0%, respectively. A closer comparison shows that TG$_X$ is more closely related to the evolutionary lineage that includes TG$_C$, TG$_E$, and band 4.2 protein than to the other transglutaminases.

The residues that make up the catalytic triad are conserved in TG$_X$ (Cys$^{277}$, His$^{336}$, Asp$^{359}$) and the core domain shows a high level of conservation as indicated by a sequence identity of about 50% between TG$_X$ and the other transglutaminases.

A Tyr residue in the barrel 1 domain of FXIIIa is hydrogen-bonded to the active site Cys residue and it has been suggested that the glutamine substrate attacks this bond to initiate the reaction based on analogy to the cysteine proteases (Yee, V. C. et al., Sem. Thromb. Haemostasis, 22: 377–384 (1996)). In TG$_X$, the Tyr residue is replaced by His$^{549}$ which is expected to be a conservative change.

Another set of hydrogen-bonded residues in factor XIIIa, His$^{342}$-Glu$^{434}$ and Asp$^{343}$-Arg$^{11}$ (located in the activation peptide), which have been suggested to guide the lysine substrate to the active site (Yee, V. C. et al., P.N.A.S. U.S.A. 91: 7296–7300 (1994)), are not conserved in that form in TG$_X$.

Crystallization experiments with FXIIIa indicated that 4 residues are involved in binding of a Ca$^{2+}$-ion, including the main chain carbonyl of Ala$^{457}$ and the side chain carboxyl groups of Asp$^{438}$, Glu$^{485}$, and Glu$^{490}$ (Yee, V. C. et al., 1996). All three acidic residues are conserved in TG$_X$ (Asp$^{401}$, Glu$^{447}$, and Glu$^{452}$)

A unique insertion of about 30 amino acids is present between the catalytic core domain and the C-terminal barrel domains in TG$_X$. A pair of oligonucleotide primers specific to this region can be used to amplify a unique fragment of TG$_X$ from genomic DNA. A preferred pair of such primers include an upstream primer having the oligonucleotide sequence TGCAGAAGCTGAAGGCTAGAAGC (SEQ ID NO:27) and a downstream primer having the sequence CCACATCACTGGGTCGAAGGGAAGG (SEQ ID NO:28), which together amplify a single 131 base pair band from human genomic DNA. These primers correspond to bases 1390–1412 and 1497–1521 of SEQ ID NO:47.

A second, smaller characteristic portion of the $TG_X$ nucleic acid sequence is found between bases 975 and 998. This sequence, which encodes amino acids 323 to 330 of SEQ ID NO:48 (RILGNKKK), evidences no substantial similarity to, or identity with, corresponding portions of the D3 domain from other known transglutaminases. These nucleic acid sequence and corresponding amino acid sequence are, therefore, also characteristic of $TG_X$.

A smaller insertion of about 10 amino acids was found in $TG_E$, and $TG_E$ has been shown to require activation by a conformational change occurring upon proteolytic cleavage in this flexible connecting loop (Kim, I. G. et al., *J. Biol. Chem.*, 268: 12682–12690 (1993)). Cleavage between these domains has also been observed in $TG_K$ and FXIIIa. While the cleaved form of $TG_K$ is highly active (Kim, S. Y. et al., *J. Biol. Chem.*, 270: 18026–18035 (1995)), contradictory results have been reported with regard to the activity of FXIIIa that has been cleaved by thrombin at this site (Takahashi, N. et al., *Proc. Natl. Acad. Sci. U.S.A.*, 83: 8019–8023 (1986); Greenberg, C. S. et al., *Biochem. J.*, 256: 1013–1019 (1988)). Proteolytic activation of transglutaminases, probably by a member of the calpain family, seems to be a common feature for the enzymes involved in epidermal differentiation (Kim, S. Y. et al., *J. Biol. Chem.*, 270: 18026–18035 (1995)), and the extended flexible (serine- and proline-rich) hinge region between the core domain and the C-terminal barrel domains in $TG_X$ should be prone to proteolytic attack.

Based on the similarity of $TG_X$ to the other active members of the transglutaminase protein family, it is likely that the characterized cDNA encodes an active transglutaminase. This is further supported by the fact that in band 4.2 protein which is the only member of this protein family without catalytic activity, the residues directly involved in the catalytic process are not conserved. The induction of $TG_X$ in differentiating keratinocytes further suggests that it might play a role in the formation of the cornified envelope. It is noted, however, that expression of $TG_X$ is not restricted to keratinocytes.

In summary, using the preferred degenerate oligonucleotides, 5 of the 6 previously characterized transglutaminases and the novel transglutaminase $TG_X$ were amplified. $TG_E$, which exhibits very restricted expression in the late stages of keratinocyte differentiation particularly in hair follicles (Kim, I. G. et al., *J. Biol. Chem.*, 268: 12682–12690 (1993)), was not detected. The expression of $TG_E$ in human epidermis has been found to be very low and not detectable in cultured human keratinocytes (Kim, I. G. et al., *J. Biol. Chem.*, 268: 12682–12690 (1993)). Besides the expected type of transglutaminase, which turned out to be the predominant type of transglutaminase in the analyzed cell types, other, apparently less abundantly expressed transglutaminases were also detected. The abundance of the PCR product for a particular type of transglutaminase correlated with its message level detected in Northern blotting, and the sum of the PCR products for all transglutaminases correlated with the measured transglutaminase activity, at least on a semi-quantitative basis.

These results suggest that the described degenerate oligonucleotides provide an excellent tool for identifying the type(s) of transglutaminase expressed in a particular cell type and for cloning of new members of this growing gene family. The homology between vertebrate and invertebrate transglutaminases is similar to the different human transglutaminases compared to each other (Aeschlimann, D. and Paulsson, M., *Thromb. Haemostasis*, 71: 402–415 (1994)) indicating that these primers may work in a wide range of different species including, but not limited to, mammalian, avian, piscis, and arthropod species in which transglutaminases are found (for review, see Aeschlimann and Paulsson, *Thromb. Haemostasis* 71: 402–415 (1994); Singer et al., *Dev. Biol.* 154: 143–159(1992); Tokunaga et al, *J. Biol. Chem.* 268: 262–268 (1993); Weraarchakul-Boonmark et al., *Proc. Natl. Acad. Sci. USA* 89: 9804–9808 (1992); Yasueda et al., *Eur. J. Biochem.* 232: 411–419 (1995)). Our results also show that many cell types express more than one type of transglutaminase which may explain some of the contradicting results in the literature.

The present invention is not intended to be limited by the preceding example, but to encompass all such modifications and variations as come within the scope of the appended claims.

SEQUENCE LISTING (1) GENERAL INFORMATION:

(iii) NUMBER OF SEQUENCES: 54

(2) INFORMATION FOR SEQ ID NO:1:

(i) SEQUENCE CHARACTERISTICS:
      (A) LENGTH: 29 base pairs
      (B) TYPE: nucleic acid
      (C) STRANDEDNESS: double
      (D) TOPOLOGY: linear (ii) MOLECULE TYPE: other nucleic acid
      (A) DESCRIPTION: /desc = "hTG-C upstream sequence"

(xi) SEQUENCE DESCRIPTION: SEQ ID NO:1:

TATGGCCAGT GCTGGGTCTT CGCCGCCGT                29

(2) INFORMATION FOR SEQ ID NO:2:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "mTG-C upstream sequence"

(xi) SEQUENCE DESCRIPTION: SEQ ID NO:2:

TACGGCCAGT GCTGGGTGTT TGCAGCGGT                29

(2) INFORMATION FOR SEQ ID NO:3:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "hTG-E upstream sequence"

(xi) SEQUENCE DESCRIPTION: SEQ ID NO:3:

TATGGCCAGT GCTGGGTCTT TGCTGGGAC                29

(2) INFORMATION FOR SEQ ID NO:4:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "mTG-E upstream sequence"

(xi) SEQUENCE DESCRIPTION: SEQ ID NO:4:

```
TTTGGCCAGT GCTGGGTGTT TGCTGGAAC                                              29
```

(2) INFORMATION FOR SEQ ID NO:5:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "hB4.2 upstream sequence"

(xi) SEQUENCE DESCRIPTION: SEQ ID NO:5:

```
GATGGCCAGG CCTGGGTGTT GGCTGCTGT                                              29
```

(2) INFORMATION FOR SEQ ID NO:6:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "mB4.2 upstream sequence"

(xi) SEQUENCE DESCRIPTION: SEQ ID NO:6:

```
GAGACCCAGG CGTGGGTGTC TGCTGCTGT                                              29
```

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "hFXIIIa upstream sequence"

(xi) SEQUENCE DESCRIPTION: SEQ ID NO:7:

TATGGCCAAT GCTGGGTTTT TGCTGGTGT                                       29

(2) INFORMATION FOR SEQ ID NO:8:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "hTG-K upstream sequence"

(xi) SEQUENCE DESCRIPTION: SEQ ID NO:8:

TATGGCCAGT GCTGGGTCTT TGCTGGCGT                                       29

(2) INFORMATION FOR SEQ ID NO:9:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "rTG-K upstream sequence"

(xi) SEQUENCE DESCRIPTION: SEQ ID NO:9:

TATGGCCAAT GCTGGGTCTT TGCTGGCGT                                       29

(2) INFORMATION FOR SEQ ID NO:10:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "hTG-P upstream sequence"

(xi) SEQUENCE DESCRIPTION: SEQ ID NO:10:

TTTGGCCAGT GCTGGGTGTT TGCTGGGAT                                       29

(2) INFORMATION FOR SEQ ID NO:11:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "rTG-P upstream sequence"

(xi) SEQUENCE DESCRIPTION: SEQ ID NO:11:

TTTGGCCAGT GCTGGGTTTT CTCTGGAGT        29

(2) INFORMATION FOR SEQ ID NO:12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "upstream consensus
            sequence"

(ix) FEATURE:
        (A) NAME/KEY: CDS
        (B) LOCATION: 1..29

(xi) SEQUENCE DESCRIPTION: SEQ ID NO:12:

TATGGCCAGT GCTGGGTNTT TGCTGGNGT        29

(2) INFORMATION FOR SEQ ID NO:13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "upstream degenerate primer
            D1"

(xi) SEQUENCE DESCRIPTION: SEQ ID NO:13:

TAYGGCCART GCTGGGTNTT YGCNGSNGT                                  29

(2) INFORMATION FOR SEQ ID NO:14:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "hTG-C downstream sequence"

(xi) SEQUENCE DESCRIPTION: SEQ ID NO:14:

TGGATGACCA GGCCGGACCT GCAGCCGGG                                  29

(2) INFORMATION FOR SEQ ID NO:15:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "mTG-C downstream sequence"

(xi) SEQUENCE DESCRIPTION: SEQ ID NO:15:

TGGATGACCA GGCCAGACCT ACAGCCGGG                                  29

(2) INFORMATION FOR SEQ ID NO:16:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "hTG-E downstream sequence"

(xi) SEQUENCE DESCRIPTION: SEQ ID NO:16:

TGGTTTGTGA GGTCTGACCT GGGCCCCCC                                             29

(2) INFORMATION FOR SEQ ID NO:17:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "mTG-E downstream sequence"

(xi) SEQUENCE DESCRIPTION: SEQ ID NO:17:

TGGTTCGTGC GGACTGACCT AGGCCCCAC                                             29

(2) INFORMATION FOR SEQ ID NO:18:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "hB4.2 downstream sequence"

(xi) SEQUENCE DESCRIPTION: SEQ ID NO:18:

TGGATGACGC GGCCTGCCTT GCCCCAGGG                                             29

(2) INFORMATION FOR SEQ ID NO:19:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "mB4.2 downstream sequence"

(xi) SEQUENCE DESCRIPTION: SEQ ID NO:19:

TGGATGAACA GACCTGATTT GTCCCAAGG                                            29

(2) INFORMATION FOR SEQ ID NO:20:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "hFXIIIa downstream
            sequence"

(xi) SEQUENCE DESCRIPTION: SEQ ID NO:20:

TGGATGACAA GGCCTGACCT TCCTGTTGG                                            29

(2) INFORMATION FOR SEQ ID NO:21:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "rTG-K downstream sequence"

(xi) SEQUENCE DESCRIPTION: SEQ ID NO:21:

TGGATGAAGA GGCCGGATCT GCCCTCGGG                                            29

(2) INFORMATION FOR SEQ ID NO:22:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "rTG-K downstream sequence"

(xi) SEQUENCE DESCRIPTION: SEQ ID NO:22:

TGGATGAAGA GGCCAGATCT GCCCTCAGG                29

(2) INFORMATION FOR SEQ ID NO:23:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "hTG-P downstream sequence"

(xi) SEQUENCE DESCRIPTION: SEQ ID NO:23:

TGGATGAAGC GACCCTACGA CGGCTGCAG                29

(2) INFORMATION FOR SEQ ID NO:24:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "rTG-P downstream sequence"

(xi) SEQUENCE DESCRIPTION: SEQ ID NO:24:

TGGATGAAAA GACAGGATCT ACCCCAGGG                29

(2) INFORMATION FOR SEQ ID NO:25:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "downstream consensus
            sequence"

(xi) SEQUENCE DESCRIPTION: SEQ ID NO:25:

```
TGGATGANGA GGCCNGACCT GCNCNNNGG                                        29
```

(2) INFORMATION FOR SEQ ID NO:26:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "downstream degenerate
            primer D2"

(xi) SEQUENCE DESCRIPTION: SEQ ID NO:26:

```
CCNGGGNGHA GRTCAGNYCT YKYCATCCA                                        29
```

(2) INFORMATION FOR SEQ ID NO:27:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "TG-X specific upstream
            primer"

(xi) SEQUENCE DESCRIPTION: SEQ ID NO:27:

```
TGCAGAAGCT GAAGGCTAGA AGC                                              23
```

(2) INFORMATION FOR SEQ ID NO:28:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "TG-X specific downstream
            primer"

(xi) SEQUENCE DESCRIPTION: SEQ ID NO:28:

CCACATCACT GGGTCGAAGG GAAGG                                    25

(2) INFORMATION FOR SEQ ID NO:29:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

Leu Phe Asn Pro Trp Cys
  1               5

(2) INFORMATION FOR SEQ ID NO:30:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

Gln Cys Trp Val Phe Ala
  1               5

(2) INFORMATION FOR SEQ ID NO:31:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:31:

```
    Trp Asn Phe His Val Trp
    1               5
```

(2) INFORMATION FOR SEQ ID NO:32:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:32:

```
    Trp Gln Xaa Leu Asp Ala Thr Pro Gln Glu
    1               5                   10
```

(2) INFORMATION FOR SEQ ID NO:33:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:33:

```
    Phe Xaa Leu Leu Phe Asn Pro Trp Cys
    1               5
```

(2) INFORMATION FOR SEQ ID NO:34:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer D3"

(xi) SEQUENCE DESCRIPTION: SEQ ID NO:34:

```
CTCTCYTCNN CNSWNCCYTC TGGGWAYTTG TA                              32
```

(2) INFORMATION FOR SEQ ID NO:35:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer D4"

(xi) SEQUENCE DESCRIPTION: SEQ ID NO:35:

```
TGGANNANGA RGANGAGMGR SARGARTATG T                               31
```

(2) INFORMATION FOR SEQ ID NO:36:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer S1"

(xi) SEQUENCE DESCRIPTION: SEQ ID NO:36:

```
TAGATGAGTA TTATGACAAC ACAGGCAGG                                  29
```

(2) INFORMATION FOR SEQ ID NO:37:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer s2"

(xi) SEQUENCE DESCRIPTION: SEQ ID NO:37:

```
AGGATTTTGG GGAATAAGAA GAAGGATAC                                  29
```

(2) INFORMATION FOR SEQ ID NO:38:

(i) SEQUENCE CHARACTERISTICS:
       (A) LENGTH: 29 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "primer s3"

(xi) SEQUENCE DESCRIPTION: SEQ ID NO:38:

TCCTTCTTCT TATTCCCCAA AATCCTGCC                              29

(2) INFORMATION FOR SEQ ID NO:39:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "primer S4"

(xi) SEQUENCE DESCRIPTION: SEQ ID NO:39:

TTCACCAGGA CACGAGTTCT GTTGGCA                                27

(2) INFORMATION FOR SEQ ID NO:40:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "primer S5"

(xi) SEQUENCE DESCRIPTION: SEQ ID NO:40:

CAAAGAGCAT CCAGAGTGAC GAGCGGG                                27

(2) INFORMATION FOR SEQ ID NO:41:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer S6"

(xi) SEQUENCE DESCRIPTION: SEQ ID NO:41:

TCTGTGGCTG GGTCAGTCTG GAAGTGC                                              27

(2) INFORMATION FOR SEQ ID NO:42:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer S7"

(xi) SEQUENCE DESCRIPTION: SEQ ID NO:42:

TGTCNATAGT TNCAGGGANA TGGGCGG                                              27

(2) INFORMATION FOR SEQ ID NO:43:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer S8"

(xi) SEQUENCE DESCRIPTION: SEQ ID NO:43:

CAGTTCTTGC TGCCTTGGTA GATGAAGCC                                            29

(2) INFORMATION FOR SEQ ID NO:44:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer S9"

(xi) SEQUENCE DESCRIPTION: SEQ ID NO:44:

GGGCTGTCCT GGCTCAGTGA TGTGGGC                          27

(2) INFORMATION FOR SEQ ID NO:45:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo(dT)-NotI
            unidirectional primer"

(xi) SEQUENCE DESCRIPTION: SEQ ID NO:45:

AACCCGGCTC GAGCGGCCGC T                                  21

(2) INFORMATION FOR SEQ ID NO:46:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "abridged anchor primer"

(xi) SEQUENCE DESCRIPTION: SEQ ID NO:46:

GGCCACGCGT CGACTAGTAC GGGNNGGGNN GGGNNG                36

(2) INFORMATION FOR SEQ ID NO:47:

(i) SEQUENCE CHARACTERISTICS:
      (A) LENGTH: 2204 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 9..2171

(ix) FEATURE:
      (A) NAME/KEY: misc_feature
      (B) LOCATION: 198..504
      (D) OTHER INFORMATION: /note= "This sequence is missing in
          TGx short form as a result of differential splicing"

(xi) SEQUENCE DESCRIPTION: SEQ ID NO:47:

```
CAGCTACC ATG GCC CAA GGG CTA GAA GTG GCC CTC ACA GAC CTC CAG AGC           50
         Met Ala Gln Gly Leu Glu Val Ala Leu Thr Asp Leu Gln Ser
          1               5                  10

TCC AGA AAT AAT GTG CGG CAC CAC ACG GAG GAG ATC ACT GTG GAC CAC            98
Ser Arg Asn Asn Val Arg His His Thr Glu Glu Ile Thr Val Asp His
 15                  20                  25                  30

CTG CTT GTT CGC CGG GGC CAG GCC TTC AAC CTC ACC CTG TAC TTC AGG           146
Leu Leu Val Arg Arg Gly Gln Ala Phe Asn Leu Thr Leu Tyr Phe Arg
                     35                  40                  45

AAC CGG AGC TTC CAG CCA GGC CTG GAC AAC ATC ATC TTC GTG GTT GAA           194
Asn Arg Ser Phe Gln Pro Gly Leu Asp Asn Ile Ile Phe Val Val Glu
             50                  55                  60

ACT GGA CCG CTG TCA GAC CTG GCC TTG GGG ACT CGG GCT GTG TTC AGC           242
Thr Gly Pro Leu Ser Asp Leu Ala Leu Gly Thr Arg Ala Val Phe Ser
         65                  70                  75

CTG GCA CGC CAT CAC AGC CCC AGC CCC TGG ATT GCC TGG CTG GAG ACC           290
Leu Ala Arg His His Ser Pro Ser Pro Trp Ile Ala Trp Leu Glu Thr
     80                  85                  90

AAT GGG GCC ACC TCC ACA GAG GTG AGC TTG TGC GCT CCT CCC ACG GCG           338
Asn Gly Ala Thr Ser Thr Glu Val Ser Leu Cys Ala Pro Pro Thr Ala
 95                 100                 105                 110

GCC GTG GGT CGG TAC CTC TTG AAA ATC CAC ATC GAC TCC TTC CAG GGG           386
Ala Val Gly Arg Tyr Leu Leu Lys Ile His Ile Asp Ser Phe Gln Gly
                115                 120                 125
```

-continued

| | |
|---|---|
| TCT GTG ACG GCC TAC CAG CTA GGG GAG TTC ATC CTG CTT TTC AAT CCC<br>Ser Val Thr Ala Tyr Gln Leu Gly Glu Phe Ile Leu Leu Phe Asn Pro<br>130              135              140 | 434 |
| TGG TGC CCA GAG GAT GCT GTC TAC TTG GAC AGT GAA CCC CAG AGG CAG<br>Trp Cys Pro Glu Asp Ala Val Tyr Leu Asp Ser Glu Pro Gln Arg Gln<br>145              150              155 | 482 |
| GAG TAT GTC ATG AAT GAT TAT GGC TTC ATC TAC CAA GGC AGC AAG AAC<br>Glu Tyr Val Met Asn Asp Tyr Gly Phe Ile Tyr Gln Gly Ser Lys Asn<br>160              165              170 | 530 |
| TGG ATC CGC CCA TGT CCC TGG AAC TAT GGA CAG TTT GAA GAC AAA ATC<br>Trp Ile Arg Pro Cys Pro Trp Asn Tyr Gly Gln Phe Glu Asp Lys Ile<br>175              180              185              190 | 578 |
| ATA GAC ATC TGC CTG AAG CTG CTA GAC AAG AGC CTG CAC TTC CAG ACT<br>Ile Asp Ile Cys Leu Lys Leu Leu Asp Lys Ser Leu His Phe Gln Thr<br>195              200              205 | 626 |
| GAC CCA GCC ACA GAC TGT GCT CTG CGG GGA AGC CCC GTC TAC GTC AGC<br>Asp Pro Ala Thr Asp Cys Ala Leu Arg Gly Ser Pro Val Tyr Val Ser<br>210              215              220 | 674 |
| AGA GTG GTG TGT GCC ATG ATC AAC AGC AAT GAT GAT AAT GGG GTG CTC<br>Arg Val Val Cys Ala Met Ile Asn Ser Asn Asp Asp Asn Gly Val Leu<br>225              230              235 | 722 |
| AAT GGA AAC TGG AGT GAG AAT TAC ACA GAC GGC GCC AAC CCT GCG GAG<br>Asn Gly Asn Trp Ser Glu Asn Tyr Thr Asp Gly Ala Asn Pro Ala Glu<br>240              245              250 | 770 |
| TGG ACG GGC AGC GTG GCC ATC CTG AAG CAG TGG AAC GCC ACA GGC TGC<br>Trp Thr Gly Ser Val Ala Ile Leu Lys Gln Trp Asn Ala Thr Gly Cys<br>255              260              265              270 | 818 |
| CAG CCC GTG CGC TAC GGG CAA TGC TGG GTC TTT GCT GCC GTC ATG TGC<br>Gln Pro Val Arg Tyr Gly Gln Cys Trp Val Phe Ala Ala Val Met Cys<br>275              280              285 | 866 |
| ACA GTG ATG AGG TGT CTG GGG ATC CCT ACC CGT GTG ATC ACC AAC TTC<br>Thr Val Met Arg Cys Leu Gly Ile Pro Thr Arg Val Ile Thr Asn Phe<br>290              295              300 | 914 |
| GAC TCT GGC CAC GAT ACA GAT GGA AAC CTG ATC ATA GAT GAG TAT TAT<br>Asp Ser Gly His Asp Thr Asp Gly Asn Leu Ile Ile Asp Glu Tyr Tyr<br>305              310              315 | 962 |
| GAC AAC ACA GGC AGG ATT TTG GGG AAT AAG AAG AAG GAT ACT ATC TGG<br>Asp Asn Thr Gly Arg Ile Leu Gly Asn Lys Lys Lys Asp Thr Ile Trp<br>320              325              330 | 1010 |
| AAC TTC CAT GTC TGG AAT GAG TGC TGG ATG GCC CGG AAG GAT CTG CCC | 1058 |

-continued

```
Asn Phe His Val Trp Asn Glu Cys Trp Met Ala Arg Lys Asp Leu Pro
335                 340                 345                 350

CCT GCA TAT GGA GGC TGG CAG GTG CTG GAC GCC ACA CCT CAG GAG ATG    1106
Pro Ala Tyr Gly Gly Trp Gln Val Leu Asp Ala Thr Pro Gln Glu Met
                        355                 360                 365

AGC AAC GGC GTC TAC TGC TGT GGC CCT GCC TCT GTC AGA GCC ATC AAA    1154
Ser Asn Gly Val Tyr Cys Cys Gly Pro Ala Ser Val Arg Ala Ile Lys
                370                 375                 380

GAA GGA GAA GTG GAC CTG AAC TAT GAC ACG CCC TTT GTG TTT TCG ATG    1202
Glu Gly Glu Val Asp Leu Asn Tyr Asp Thr Pro Phe Val Phe Ser Met
            385                 390                 395

GTG AAT GCT GAC TGC ATG TCC TGG CTC GTC CAG GGA GGG AAG GAG CAG    1250
Val Asn Ala Asp Cys Met Ser Trp Leu Val Gln Gly Gly Lys Glu Gln
        400                 405                 410

AAG CTT CAC CAG GAC ACG AGT TCT GTT GGC AAT TTT ATC AGC ACA AAG    1298
Lys Leu His Gln Asp Thr Ser Ser Val Gly Asn Phe Ile Ser Thr Lys
415                 420                 425                 430

AGC ATC CAG AGT GAC GAG CGG GAT GAC ATC ACA GAG AAC TAC AAG TAT    1346
Ser Ile Gln Ser Asp Glu Arg Asp Asp Ile Thr Glu Asn Tyr Lys Tyr
                435                 440                 445

GAA GAA GGA TCC CTC CAG GAG AGG CAG GTG TTT CTG AAG GCT CTG CAG    1394
Glu Glu Gly Ser Leu Gln Glu Arg Gln Val Phe Leu Lys Ala Leu Gln
                450                 455                 460

AAG CTG AAG GCT AGA AGC TTC CAT GGC TCC CAA AGA GGA GCA GAG TTG    1442
Lys Leu Lys Ala Arg Ser Phe His Gly Ser Gln Arg Gly Ala Glu Leu
            465                 470                 475

CAA CCT TCC AGG CCC ACA TCA CTG AGC CAG GAC AGC CCT CGG AGC CTG    1490
Gln Pro Ser Arg Pro Thr Ser Leu Ser Gln Asp Ser Pro Arg Ser Leu
        480                 485                 490

CAT ACA CCT TCC CTT CGA CCC AGT GAT GTG GTG CAA GTC TCC CTG AAA    1538
His Thr Pro Ser Leu Arg Pro Ser Asp Val Val Gln Val Ser Leu Lys
495                 500                 505                 510

TTC AAG CTG CTC GAC CCG CCC AAC ATG GGC CAG GAT ATA TGC TTT GTC    1586
Phe Lys Leu Leu Asp Pro Pro Asn Met Gly Gln Asp Ile Cys Phe Val
                515                 520                 525

CTG CTG GCC CTC AAC ATG TCC TCC CAG TTC AAG GAC CTC AAA GTG AAC    1634
Leu Leu Ala Leu Asn Met Ser Ser Gln Phe Lys Asp Leu Lys Val Asn
                530                 535                 540

CTG AGT GCC CAG TCT CTG CTG CAC GAT GGC AGC CCC CTG TCC CCA TTC    1682
Leu Ser Ala Gln Ser Leu Leu His Asp Gly Ser Pro Leu Ser Pro Phe
            545                 550                 555
```

```
TGG CAG GAC ACA GCG TTC ATC ACA CTC TCT CCT AAA GAA GCA AAG ACC     1730
Trp Gln Asp Thr Ala Phe Ile Thr Leu Ser Pro Lys Glu Ala Lys Thr
560                 565                 570

TAC CCC TGC AAA ATC TCC TAT TCC CAG TAC AGC CAG TAC CTG TCA ACA     1778
Tyr Pro Cys Lys Ile Ser Tyr Ser Gln Tyr Ser Gln Tyr Leu Ser Thr
575                 580                 585                 590

GAC AAG CTG ATC CGC ATC AGT GCC CTG GGT GAA GAG AAA AGC AGT CCT     1826
Asp Lys Leu Ile Arg Ile Ser Ala Leu Gly Glu Glu Lys Ser Ser Pro
                595                 600                 605

GAG AAA ATC CTG GTG AAC AAG ATC ATC ACC TTA TCT TAT CCA AGC ATC     1874
Glu Lys Ile Leu Val Asn Lys Ile Ile Thr Leu Ser Tyr Pro Ser Ile
            610                 615                 620

ACG ATT AAT GTT CTA GGA GCA GCC GTT GTG AAC CAG CCA CTC TCC ATA     1922
Thr Ile Asn Val Leu Gly Ala Ala Val Val Asn Gln Pro Leu Ser Ile
        625                 630                 635

CAG GTG ATA TTT TCA AAC CCC CTC TCG GAG CAG GTT GAG GAC TGT GTG     1970
Gln Val Ile Phe Ser Asn Pro Leu Ser Glu Gln Val Glu Asp Cys Val
    640                 645                 650

CTG ACT GTG GAA GGA AGT GGC CTC TTC AAG AAA CAG CAG AAA GTC TTC     2018
Leu Thr Val Glu Gly Ser Gly Leu Phe Lys Lys Gln Gln Lys Val Phe
655                 660                 665                 670

CTT GGA GTC CTC AAA CCC CAA CAC CAA GCA AGC ATT ATT CTG GAG ACC     2066
Leu Gly Val Leu Lys Pro Gln His Gln Ala Ser Ile Ile Leu Glu Thr
                675                 680                 685

GTC CCC TTC AAG AGT GGA CAA AGG CAG ATC CAA GCT AAT ATG AGA AGC     2114
Val Pro Phe Lys Ser Gly Gln Arg Gln Ile Gln Ala Asn Met Arg Ser
            690                 695                 700

AAC AAG TTT AAG GAC ATT AAG GGT TAC AGG AAT GTT TAT GTA GAC TTT     2162
Asn Lys Phe Lys Asp Ile Lys Gly Tyr Arg Asn Val Tyr Val Asp Phe
        705                 710                 715

GCA TTA TAA ATTCTGGAAC AACGCGCCAG ACGTGTGAGT TTC                    2204
Ala Leu *
720

(2) INFORMATION FOR SEQ ID NO:48:

(i) SEQUENCE CHARACTERISTICS:
        (A) LENGTH: 721 amino acids
        (B) TYPE: amino acid
        (D) TOPOLOGY: linear
```

(ii) MOLECULE TYPE: protein (xi) SEQUENCE DESCRIPTION: SEQ ID NO:48:

Met Ala Gln Gly Leu Glu Val Ala Leu Thr Asp Leu Gln Ser Ser Arg
 1               5                  10                  15

Asn Asn Val Arg His His Thr Glu Glu Ile Thr Val Asp His Leu Leu
            20                  25                  30

Val Arg Arg Gly Gln Ala Phe Asn Leu Thr Leu Tyr Phe Arg Asn Arg
        35                  40                  45

Ser Phe Gln Pro Gly Leu Asp Asn Ile Ile Phe Val Val Glu Thr Gly
    50                  55                  60

Pro Leu Ser Asp Leu Ala Leu Gly Thr Arg Ala Val Phe Ser Leu Ala
65                  70                  75                  80

Arg His His Ser Pro Ser Pro Trp Ile Ala Trp Leu Glu Thr Asn Gly
                85                  90                  95

Ala Thr Ser Thr Glu Val Ser Leu Cys Ala Pro Pro Thr Ala Ala Val
            100                 105                 110

Gly Arg Tyr Leu Leu Lys Ile His Ile Asp Ser Phe Gln Gly Ser Val
        115                 120                 125

Thr Ala Tyr Gln Leu Gly Glu Phe Ile Leu Leu Phe Asn Pro Trp Cys
    130                 135                 140

Pro Glu Asp Ala Val Tyr Leu Asp Ser Glu Pro Gln Arg Gln Glu Tyr
145                 150                 155                 160

Val Met Asn Asp Tyr Gly Phe Ile Tyr Gln Gly Ser Lys Asn Trp Ile
                165                 170                 175

Arg Pro Cys Pro Trp Asn Tyr Gly Gln Phe Glu Asp Lys Ile Ile Asp
            180                 185                 190

Ile Cys Leu Lys Leu Leu Asp Lys Ser Leu His Phe Gln Thr Asp Pro
        195                 200                 205

Ala Thr Asp Cys Ala Leu Arg Gly Ser Pro Val Tyr Val Ser Arg Val
    210                 215                 220

Val Cys Ala Met Ile Asn Ser Asn Asp Asp Asn Gly Val Leu Asn Gly
225                 230                 235                 240

Asn Trp Ser Glu Asn Tyr Thr Asp Gly Ala Asn Pro Ala Glu Trp Thr
                245                 250                 255

Gly Ser Val Ala Ile Leu Lys Gln Trp Asn Ala Thr Gly Cys Gln Pro
            260                 265                 270

Val Arg Tyr Gly Gln Cys Trp Val Phe Ala Ala Val Met Cys Thr Val
        275                 280                 285

Met Arg Cys Leu Gly Ile Pro Thr Arg Val Ile Thr Asn Phe Asp Ser
    290                 295                 300

Gly His Asp Thr Asp Gly Asn Leu Ile Ile Asp Glu Tyr Tyr Asp Asn
305                 310                 315                 320

Thr Gly Arg Ile Leu Gly Asn Lys Lys Lys Asp Thr Ile Trp Asn Phe
                325                 330                 335

His Val Trp Asn Glu Cys Trp Met Ala Arg Lys Asp Leu Pro Pro Ala
            340                 345                 350

Tyr Gly Gly Trp Gln Val Leu Asp Ala Thr Pro Gln Glu Met Ser Asn
        355                 360                 365

Gly Val Tyr Cys Cys Gly Pro Ala Ser Val Arg Ala Ile Lys Glu Gly
    370                 375                 380

Glu Val Asp Leu Asn Tyr Asp Thr Pro Phe Val Phe Ser Met Val Asn
385                 390                 395                 400

Ala Asp Cys Met Ser Trp Leu Val Gln Gly Gly Lys Glu Gln Lys Leu
                405                 410                 415

His Gln Asp Thr Ser Ser Val Gly Asn Phe Ile Ser Thr Lys Ser Ile
            420                 425                 430

Gln Ser Asp Glu Arg Asp Asp Ile Thr Glu Asn Tyr Lys Tyr Glu Glu
        435                 440                 445

Gly Ser Leu Gln Glu Arg Gln Val Phe Leu Lys Ala Leu Gln Lys Leu
    450                 455                 460

Lys Ala Arg Ser Phe His Gly Ser Gln Arg Gly Ala Glu Leu Gln Pro
465                 470                 475                 480

Ser Arg Pro Thr Ser Leu Ser Gln Asp Ser Pro Arg Ser Leu His Thr
                485                 490                 495

Pro Ser Leu Arg Pro Ser Asp Val Val Gln Val Ser Leu Lys Phe Lys
        500                 505                 510

Leu Leu Asp Pro Pro Asn Met Gly Gln Asp Ile Cys Phe Val Leu Leu
        515                 520                 525

Ala Leu Asn Met Ser Ser Gln Phe Lys Asp Leu Lys Val Asn Leu Ser
        530                 535                 540

Ala Gln Ser Leu Leu His Asp Gly Ser Pro Leu Ser Pro Phe Trp Gln
545                 550                 555                 560

Asp Thr Ala Phe Ile Thr Leu Ser Pro Lys Glu Ala Lys Thr Tyr Pro
                565                 570                 575

Cys Lys Ile Ser Tyr Ser Gln Tyr Ser Gln Tyr Leu Ser Thr Asp Lys
                580                 585                 590

Leu Ile Arg Ile Ser Ala Leu Gly Glu Glu Lys Ser Ser Pro Glu Lys
                595                 600                 605

Ile Leu Val Asn Lys Ile Ile Thr Leu Ser Tyr Pro Ser Ile Thr Ile
        610                 615                 620

Asn Val Leu Gly Ala Ala Val Val Asn Gln Pro Leu Ser Ile Gln Val
625                 630                 635                 640

Ile Phe Ser Asn Pro Leu Ser Glu Gln Val Glu Asp Cys Val Leu Thr
                645                 650                 655

Val Glu Gly Ser Gly Leu Phe Lys Lys Gln Lys Val Phe Leu Gly
                660                 665                 670

Val Leu Lys Pro Gln His Gln Ala Ser Ile Ile Leu Glu Thr Val Pro
        675                 680                 685

Phe Lys Ser Gly Gln Arg Gln Ile Gln Ala Asn Met Arg Ser Asn Lys
        690                 695                 700

Phe Lys Asp Ile Lys Gly Tyr Arg Asn Val Tyr Val Asp Phe Ala Leu
705                 710                 715                 720

*

(2) INFORMATION FOR SEQ ID NO:49:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:49:

TGGTGCCCAG GTGAGCCACA                                                     20

(2) INFORMATION FOR SEQ ID NO:50:

(i) SEQUENCE CHARACTERISTICS:
        (A) LENGTH: 11 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:50:

CGGATGCTGT G                                                              11

(2) INFORMATION FOR SEQ ID NO:51:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:51:

TGGCTGAATG GTAGGTGTCT                                                     20

(2) INFORMATION FOR SEQ ID NO:52:

(i) SEQUENCE CHARACTERISTICS:
        (A) LENGTH: 21 base pairs
        (B) TYPE: nucleic acid

```
        (C) STRANDEDNESS: double
        (D) TOPOLOGY: linear (ii) MOLECULE TYPE: DNA (genomic)

(xi) SEQUENCE DESCRIPTION: SEQ ID NO:52:

TATCAAATAG TGGATAGCGT C                                              21

(2) INFORMATION FOR SEQ ID NO:53:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:53:

TGGAATAGAG GTAAGTTTGA                                                20

(2) INFORMATION FOR SEQ ID NO:54:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:54:

CTCTCACCAG AGGATGCTGT G                                              21
```

We claim:

1. A purified preparation of a polypeptide comprising a sequence of amino acids selected from the group consisting of amino acids 461 to 504 of SEQ ID NO:48 and amino acids 323 to 330 of SEQ ID NO:48.

2. A polypeptide as claimed in claim 1 comprising a sequence of amino acids as shown in SEQ ID NO:48.

* * * * *